United States Patent [19]
Slaugh et al.

[11] Patent Number: 5,942,656
[45] Date of Patent: Aug. 24, 1999

[54] PROCESS FOR SEPARATING LINEAR ALPHA OLEFINS FROM 2-BRANCHED AND/OR 3-BRANCHED ALPHA OLEFINS

[75] Inventors: Lynn Henry Slaugh; Laurent Alain Fenouil, both of Houston; Howard Lam-Ho Fong, Sugar Land, all of Tex.

[73] Assignee: Shell Oil Company, Houston, Tex.

[21] Appl. No.: 08/987,553

[22] Filed: Dec. 9, 1997

[51] Int. Cl.$^6$ .............................. C07C 7/00; C07C 2/64
[52] U.S. Cl. .................... 585/864; 585/446; 585/809; 585/865; 585/867
[58] Field of Search ................. 585/446, 809, 585/864, 865, 867, 448

[56] References Cited

U.S. PATENT DOCUMENTS

| | | | |
|---|---|---|---|
| 4,915,794 | 4/1990 | Slaugh et al. | 203/29 |
| 4,946,560 | 8/1990 | Slaugh et al. | 203/38 |
| 5,012,034 | 4/1991 | Weingaertner et al. | 585/806 |

OTHER PUBLICATIONS

U.S. application No. 08/987,555, Slaugh et al., filed Dec. 9, 1997.

U.S. application No. 08/876,822, Slaugh et al., filed Jun. 16, 1997.

*Primary Examiner*—Walter D. Griffin
*Assistant Examiner*—Tam M. Nguyen
*Attorney, Agent, or Firm*—Dennis V. Carmen

[57] ABSTRACT

A process for separating linear alpha olefins from branched alpha olefins in a feed stream by:

a) contacting the feed stream with a linear polyaromatic compound having at least four fused aromatic rings, such as 2,3-benzanthracene, under conditions effective to form a reaction mixture comprising a linear polyaromatic compound-linear alpha olefin adduct;

b) separating the linear polyaromatic compound-linear alpha olefin adduct from the reaction mixture;

c) dissociating the linear polyaromatic compound-linear alpha olefin adduct to form the linear polyaromatic compound and a linear alpha olefin composition, and optionally d) separating the linear polyaromatic compound formed in step c) from the linear alpha olefin composition.

19 Claims, No Drawings

PROCESS FOR SEPARATING LINEAR ALPHA OLEFINS FROM 2-BRANCHED AND/OR 3-BRANCHED ALPHA OLEFINS

1. FIELD OF THE INVENTION

This invention relates to a process for separating linear alpha olefins from 2- branched alpha olefins and/or 3-branched alpha olefins, from a mixture of olefins comprising internal olefins, linear alpha olefins, 2-branched alpha olefins, 3-branched alpha olefins, or mixtures thereof, by contacting the feed stream with linear polyaromatic compounds having 4 or more fused aromatic rings under conditions effective to form a reaction mixture comprising a linear polyaromatic compound-linear alpha olefin adduct.

2. BACKGROUND OF THE INVENTION

Many industrial processes produce olefins that are mixtures of alpha olefins and internal olefins. Due to the similarities in properties between alpha and internal olefins of the same molecular weight or overlapping carbon numbers, it is not an easy matter to separate the two. Olefins are frequently used in the manufacture of polymers or as drilling mud additives, or as intermediates for the production of oil additives and detergents. Depending upon the particular application, it would be desirable to manufacture an alpha olefin composition having the greatest purity possible. For example, polyethylene polymers are often made by copolymerizing ethylene with small amounts of a linear alpha olefin such as 1-octene. A 1-octene olefin composition containing substantial branched species, especially on the second and/or third carbon atoms, is not suited for this purpose. The olefin needed for this purpose is one in which the branched alpha olefins are removed as much as possible. While such pure species of linear alpha olefins with a narrow carbon number range can be manufactured and provided at great cost, we have found that it would be particularly desirable to economically provide the application industry with large quantities of a purified linear alpha olefin composition made from a raw feed stream containing a mixture of at least internal olefins, linear alpha olefins, and 2-branched alpha olefins. Many feed streams contain additional impurities such as alcohols, ketones, and 3-branched alpha olefins, from which the linear alpha olefins should be separated.

Separating and isolating linear non-branched alpha olefins from 2-branched alpha olefins and/or 3-branched alpha olefins is no easy task, especially when these species have similar or identical molecular weights or carbon numbers. Conventional distillation methods are inadequate to separate species of this type which have such closely related boiling points. The separation problem is further aggravated in that the linear non-branched alpha olefin species not only needs to be separated from branched alpha olefins, but also from everything else present in the feed stream mixture, such as the internal linear or branched olefins. U.S. Pat. No. 4,946,560 described a process for the separation of internal olefins from alpha olefins by contacting a feed stream with anthracene to form an olefin adduct, separating the adduct from the feed stream, heating the adduct to produce anthracene and the olefin product enriched in alpha olefin, and separating out the anthracene from the alpha olefin.

We have now discovered alternative adducting compounds besides anthracene which are effective to separate out linear alpha olefins from other olefins in a raw feed stream.

3. SUMMARY OF THE INVENTION.

This invention relates to a process for separating linear alpha olefins from branched alpha olefins. In particular, there is provided a process for treating a feed stream comprising linear alpha olefins and olefins other than linear alpha, comprising:

a) contacting the feed stream with linear polyaromatic compounds having 4 or more fused aromatic rings under conditions effective to form a reaction mixture comprising a linear polyaromatic compound-linear alpha olefin adduct;

b) separating the linear polyaromatic compound-linear alpha olefin adduct, and optionally the unreacted linear polyaromatic compound as well, from the reaction mixture;

c) dissociating the linear polyaromatic compound-linear alpha olefin adduct to form the linear polyaromatic compound and a linear alpha olefin composition, and optionally but preferably d) separating the linear polyaromatic compound formed in step c) from said linear alpha olefin composition.

In one embodiment of the invention, the linear alpha olefin stream is an olefin stream enriched in linear alpha olefins relative to the feed stream

4. DETAILED DESCRIPTION OF THE INVENTION

A linear alpha olefin(s) means the absence of branching at both the $C_2$ and the $C_3$ positions, each relative to the alpha double bond.

A branched alpha olefin(s) means an alpha olefin having a branch at least at the $C_2$ or alternatively at least at the $C_3$ position, each relative to the alpha double bond. Branches at both the $C_2$ and the $C_3$ positions are within the meaning of a branched alpha olefin, as well as branches present at additional positions beyond the $C_3$ position so long as at least one branch is present at the $C_2$ and/or $C_3$ position. Alpha olefins having branches at only the $C_3$ position, or only at the $C_2$ position, are also within the meaning of a branched alpha olefin.

The feed stream olefins used in the process of the invention comprises at least linear alpha olefins and olefins other than linear alpha olefins. In a preferable embodiment, the feed stream comprises internal olefins, branched alpha olefins, and linear alpha olefins. By internal olefins is meant linear and/or branched internal olefins. The feed stream is generally produced by commercial processes such as the oligomerization of ethylene, optionally followed by isomerization and disproportionation. Alternatively, the feed stream may be produced by the Fisher-Tropsch process, which typically contains a substantial number of branched species.

In the preferred embodiment wherein the feed stream comprises at least branched alpha olefins, internal olefins, and linear alpha olefins, the amount of each ingredient in the feed stream is not particularly limited. In fact, the feed stream may contain as little as 1 wt. % of internal olefins. However, the process of the invention is particularly suited to the large volume-industrial scale production of linear alpha olefin compositions needed in those applications which are sensitive to the presence of branched alpha olefins in an amount beyond about 3 wt. %. Accordingly, in a preferred embodiment of the invention, the feed stream contains at least 2 wt. % of branched alpha olefins, and more preferably contains 3 wt. % or more of branched alpha olefins, in the initial pass. The process of the invention will also advantageously separate the branched internal olefins, the branched alpha olefins, and the linear internal olefins from the linear alpha olefins.

In many applications, the presence of branching on a branched alpha olefin at the $C_2$ or $C_3$ position is undesirable.

Therefore, to ensure the highest product quality, in a highly preferred embodiment of the invention, the separation operation should be carried out on feed streams which contain a total of 3 wt. % or more of branched olefins, whether the olefin is internal or alpha, based on the weight of the feed stream. The invention, however, is not limited to carrying out the separation/purification steps on feed streams containing more than 3 wt. % of branched olefins. Feed streams containing as little as 1 wt. % of branched olefins or 1 wt. % of branched alpha olefins can also be successfully treated to further reduce the branched alpha olefin content where needed for some applications (and even if not particularly needed for an application). The need for treating feed stream already so low in branched olefins is not as pressing, however, since a fair portion of applications desiring pure alpha olefin compositions can tolerate these low levels of branched olefins.

Generally, the feed stream will not contain more than 85 wt % of branched alpha olefins, based on the weight of the feed stream, although the particular amount will often vary with the method of manufacturing the feed stream, such as by oligomerizing ethylene or by the Fisher-Tropsch process. Typically, the amount of branched alpha olefins present in the feed stream will not exceed 50 wt. %, based on the feed stream weight. More common amounts of branched alpha olefin in feed streams range from 5 wt. % to 40 wt. %.

The amount of branched internal olefins in the feed stream is not limited. The feed stream may contain from 0 wt. % to 30 wt. % of branched internal olefins, while amounts ranging from 1 wt. % to 15 wt. % are common.

The amount of linear internal olefins is not limited, and can range from 0.0 wt. % to 80 wt. %, with amounts ranging from 1 wt. % to 20 wt. % being common.

The amount of linear alpha olefins in the feed stream can vary widely, and may range from 5 wt. % to 97 wt. %. While the feed stream may contain less than 5 wt. % of linear alpha olefins, isolating less than 5 wt. % of linear alpha olefins obtained in the separation process may not be economically justified. The feed stream should preferably contain at least 10 wt. %, more preferably at least 15 wt. %, and most preferably at least 20 wt. % of the linear alpha olefin. In those cases where a feed stream is produced by a Fisher-Tropsch process, the feed stream will generally contain less than 50 wt. % of linear alpha olefins.

Other ingredients which may be present in the feed stream include aromatic compounds, paraffins, and oxygenated compounds. These other ingredients may be present in the feed stream in amounts ranging from 0 wt. % to 50 wt. %.

Typically the feed olefins will have an average carbon number ranging from about 4 to about 22, more preferably from about 6 to about 18. The physical properties demanded by the end use of the olefins in part determines the suitable carbon numbers to be isolated. Olefins with carbon numbers greater than 22 and lower than 6 can be utilized in the instant process, but from a commercially practical point of view, feed streams with carbon numbers ranging from about 6 to about 18 will be most frequently used. For example, linear alpha olefins having carbon numbers of 4–8 are commonly used as comonomers in the manufacture of polyethylenes, linear alpha olefins having a carbon number ranging from 8–12 are commonly used to make polyalphaolefins, and alpha olefins having carbon numbers in the range of 12–18 are used as intermediates in the manufacture of detergents.

The linear polyaromatic compound is utilized in the instant process to form the adduct with the alpha olefins in the feed stream. While not being bound to a theory, it is believed that the linear polyaromatic compound preferentially forms an adduct with the linear alpha olefins and to a lesser extent, if at all, with the 2-branched alpha olefins. The preferential adduction of linear polyaromatic compound toward the linear alpha olefin over the branched alpha olefins or internal olefins may be due to the steric hindrance and/or electronic effects of the latter olefins in a Diels-Alder reaction.

As used herein, "linear polyaromatic compound" refers to a linear polyaromatic compound having at least four fused aromatic rings. The linearity should extend to at least four consecutively fused cyclic rings. Non-limiting examples of the linear polyaromatic compound include 2,3-benzanthracene, pentacene, and hexacene. Surprisingly, we have found that non-linear polyaromatic compounds, such as 1,2-benzanthracene, failed to successfully separate out linear alpha olefins from branched alpha olefins and internal olefins. Accordingly, at least four consecutive fused cyclic rings of the compound should be in a linear orientation, with the compound containing at least four fused aromatic rings. Preferably, the four consecutive fused cyclic rings are aromatic rings.

The linear polyaromatic compound may be substituted or unsubstituted. The phrase linear polyaromatic compound also refers to pure compounds or compositions containing as one of their ingredients the linear polyaromatic compound, including but not limited to coal tars containing linear polyaromatic compound, linear polyaromatic compound oils, and any crude mixtures containing cuts separated from naphthalene.

Suitable examples of substituents on substituted linear polyaromatic compounds include, but are not limited to, lower alkyl, e.g., methyl, ethyl, butyl; halo, e.g., chloro, bromo, fluoro; nitro; sulfato; sulfonyloxy; carboxyl; carbolower-alkoxy, e.g., carbomethoxy, carbethoxy; amino; mono- and di-lower-alkylamino, e.g., methylamino, dimethylamino, methylethylamino; amido; hydroxy; cyano; lower-alkoxy, e.g., methoxy, ethoxy; lower-alkyanoyloxy, e.g., acteoxy; monocyclic aryls, e.g., phenyl, xylyl, toluyl, benzyl, etc. The particular substituent size, their number, and their location, should be selected so that they are relatively inert under the reaction conditions and relatively small to avoid sterically hindering the formation of the Diels-Alder adduct. Suitable substituted linear polyaromatic compounds can be determined by routine experimentation. The preferred linear polyaromatic compound is 2,3-benzanthracene.

The linear polyaromatic compound also includes aromatic molecules linked together by a bridging group, such as a hydrocarbon chain, an ether linkage, or a ketone group containing chain.

The process of the instant invention is basically a three step process wherein (a) linear polyaromatic compound is reacted with an olefin composition to form an adduct, (b) the adduct is separated from the reaction mixture, and (c) the adduct is dissociated to release the olefin and regenerate the linear polyaromatic compound. The Diels-Alder adduct forming reaction is carried out in a conventional fashion and reaction zone. An example of a suitable reaction zone is a continuously stirred tank reactor wherein olefin and linear polyaromatic compound are added continuously to a stirred tank, and the reaction mixture is continuous withdrawn from the stirred tank. Alternatively, the reaction may be carried out in a batch reactor, wherein the olefin and the linear polyaromatic compound are charged to an autoclave which is then heated to a reaction temperature sufficient to complete the reaction. The reaction is typically carried out over a range of temperatures from about 150° to about 290° C., preferably from about 200° to about 280° C., and most preferably from about 240° to about 265° C. Pressures are not critical and typically run from about atmospheric to about 100 atmospheres. The reaction can be carried out in the gas phase under vacuum or liquid phase or mixed gas-liquid phase, depending on the volatility of the feed olefins, but generally in the liquid phase.

Stoichiometric proportions or an excess of either olefin or linear polyaromatic compound can be used in forming the adducts, but a molar excess of olefin is preferred. The molar ratio of olefin to linear polyaromatic compound is preferably from greater than 0.5:1 up to 10:1, more preferably from 1.5:1 to 7:1.

An inert solvent can be utilized to dissolve the feed olefins or the linear polyaromatic compound or both in the reactor. Preferred solvents are the hydrocarbon solvents which are liquid at reaction temperatures and in which the olefins, linear polyaromatic compound and olefin-linear polyaromatic compound adducts are soluble. Illustrative examples of useful solvents include the alkanes such as pentane, iso-pentane, hexane, heptane, octane, nonane, and the like; cycloalkanes such as cyclopentane, cyclohexane, and the like; and aromatics such as benzene, toluene, ethylbenzene, diethylbenzene, and the like. The amount of solvent to be employed can vary over a wide range without a deleterious effect on the reaction.

In one embodiment of the invention, however, the feed stream and linear polyaromatic compound-linear alpha olefin adduct formation is carried out in the absence of a solvent. We have found that the absence of a solvent does not substantially affect the amount of linear polyaromatic compound regenerated under equivalent reaction conditions, and that the concentration of linear alpha olefins generated is substantially the same. Thus, in a preferred embodiment, the process of the invention is conducted in the absence of a solvent.

After the linear polyaromatic compound-olefin adduct has been formed, it is separated from the reaction mixture. The olefin-linear polyaromatic compound adduct is separated from the reaction mixture by conventional means. Due to the large molecular weight and structural difference between the linear polyaromatic compound-linear alpha olefin adduct and the remainder of the reaction mixture, conventional separation techniques are quite suitable for removing the unreacted olefins from the linear polyaromatic compound-linear alpha olefin adduct. For example, the unreacted olefins may be removed at the overhead or in fractions by vacuum or flash distillation of the reaction mixture to leave the linear polyaromatic compound-linear alpha olefin adduct and unreacted linear polyaromatic compound as a bottoms. The other unreacted components of the reaction mixture, such as the unreacted olefins, including branched and linear internal olefins, 2-branched alpha olefins and/or 3-branched alpha olefins, as well as paraffins, aromatics, alcohols, ketones, acids, and other impurities may be distilled off. Alternatively, the linear polyaromatic compound-linear alpha olefin adduct is separated by cooling the reaction mixture until the adduct crystallizes out, followed by filtration or centrifugation to remove the unreacted olefin. In most cases the unreacted linear polyaromatic compound will separate out with the linear polyaromatic compound-linear alpha olefin adduct. The remainder of the reaction mixture can be used in other processes or applications since is will have an enriched internal olefin content over that of the feed stream.

The next step of the instant process is to dissociate the linear polyaromatic compound-linear alpha olefin adduct.

The dissociation process can be accomplished by heating or pyrolyzing the recovered linear polyaromatic compound-linear alpha olefin adduct at a temperature of from about 250° to about 400° C., preferably from about 300° to about 350° C. This pyrolysis frees the linear alpha olefins from the linear polyaromatic compound. The linear polyaromatic compound is then separated from the resulting mixture by any conventional means, which may occur simultaneously with the pyrolysis operation, such as by vacuum or flash distilling off the linear alpha olefins along with any impurities at the pyrolysis temperatures, and removing the linear polyaromatic compound as a bottoms from the adduct dissociating reactor. Other separation techniques include filtration and centrifugation. The linear polyaromatic compound may be recycled back to the adduct reaction zone. The separated linear alpha olefin composition is enriched in linear alpha olefin content over that of the feed stream, and the concentration of the branched alpha olefins in the linear alpha olefin composition is reduced over that of the feed stream.

While most of the branched alpha olefins will have been separated from the linear alpha olefins, a small amount of branched alpha olefins, along with other impurities, may be present in the linear alpha olefin composition after only one pass. For many applications, the amount of branched alpha olefins in the linear alpha olefin composition after one pass through the process of the invention is sufficiently small that only one pass through the process is necessary. If desired, however, the linear alpha olefin composition may be subjected to multiple passes through additional reaction zones and adduct dissociating reactors fed by the linear alpha olefin composition produced from the prior pass, to further reduce the branched alpha olefin content and further enhance the linear alpha olefin content. In a preferred embodiment, the process of the invention is repeated more than once, more preferably 2–4 times.

The amount of branched alpha olefins in the linear alpha olefin composition is less than 4 wt. % after subjecting the feed stream to the process of the invention. Preferably, the amount of branched alpha olefins, especially the amount of 2-branched alpha olefin, in the linear alpha olefin composition is 3 wt. % or less. With multiple passes, the content of the branched alpha olefins, and especially the amount of 2-branched alpha olefins, can be reduced in the linear alpha olefin composition to 3.0 wt. % or less, more preferably 2.0 wt. % or less, most preferably 1.0 wt. % or less.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result is intended to be within the scope of the instant invention.

The present invention will now be illustrated by means of the following illustrative embodiments and examples which are provided for illustration and are not to be construed as limiting the invention.

EXAMPLE 1

To illustrate the concept of the invention, an eight carbon olefin composition was used as the feed stream. 0.035 moles of an olefin feed stream having a composition as identified in Table 1 below, along with 0.0175 moles of 2,3-benzanthracene, were charged to a 100 ml. Parr autoclave. The autoclave was purged three times with nitrogen and sealed. The autoclave was placed in a dry box and a nitrogen purged feed stream was added to the autoclave along with 20 ml. of dry, nitrogen-purged toluene. The autoclave was sealed, removed from the dry box, placed in a heating mantle and heated to 255° C. for 2 hours. The autoclave contents were stirred during heating. The autoclave was then cooled to 20° C. The unreacted, excess olefin feed stream was removed by distillation from the product mixture. The remaining unconverted 2,3-benzanthracene and the 2,3-benzanthracene-linear alpha olefin adduct mixture was then heated to 300–350° C. for about 0.5 hours, during which time the 2,3-benzanthracene-linear alpha olefin adduct dissociated to recyclable 2,3-benzanthracene and the alpha olefin product enriched in 1-octene content. This run is designated as run 1.

The same procedure was followed as employed in run 1, except that the adducting compound used was 1,2-benzanthracene. This run is designated as run 2.

This linear alpha olefin compositions of runs 1 and 2 were analyzed by gas chromatography. The results are shown in Table 1. The concentration of the species within the feed stream and within the resulting linear alpha olefin composition is measured by mole percent.

TABLE 1

| Run Number | 2,3-Benzan-thracene moles | 1,2-Benzan-thracene moles | 2,3-Benzan-thracene Conversion % | 2-Methyl-1-heptene mole % | 1-Octene mole % | Trans-4-octene mole % | Trans-2-octene mole % | Olefin Recovery % |
|---|---|---|---|---|---|---|---|---|
| | Feedstream Composition | | | 7.8 | 72.1 | 9.6 | 10.5 | |
| 1 | .0175 | — | 54.6 | 3.6 | 84.8 | 3.2 | 6.4 | 94 |
| 2 | — | .0175 | 0 | 0 | 0 | 0 | 0 | 0 |

The results tabulated in Table 1 indicate that the process of the invention successfully separated out the 2-branched alpha olefins from the linear alpha olefins, and produced an olefin stream enriched in linear alpha olefins. As can be seen from the results, the mole percent of the 2-methyl-1-heptene branched alpha olefins was substantially reduced from the amount contained in the feed streams, and the mole percent of the desired linear alpha olefin 1-octene was substantially raised over that of the feed stream.

Comparison of runs 1 and 2 also indicates that the non-linear 1,2-benzanthracene was not successful at separating the linear alpha olefins or producing an olefin stream enriched in linear alpha olefins. The 1,2-benzanthracene failed to form an adduct with the olefins.

What we claim is:

1. A process for treating a feed stream comprising linear alpha olefins and olefins other than linear alpha, comprising:
   a) contacting the feed stream with linear polyaromatic compounds having 4 or more fused aromatic rings under conditions effective to form a reaction mixture comprising a linear polyaromatic compound-linear alpha olefin adduct;
   b) separating the linear polyaromatic compound-linear alpha olefin adduct from the reaction mixture; and
   c) dissociating the linear polyaromatic compound-linear alpha olefin adduct to form the linear polyaromatic compound and a linear alpha olefin composition, and optionally
   d) separating the linear polyaromatic compound formed in step c) from said linear alpha olefin composition.

2. The process of claim 1, wherein the feed stream is contacted with the linear polyaromatic compound at a temperature ranging from 150° to about 290° C.

3. The process of claim 2, wherein the feed stream is contacted with the linear polyaromatic compound at a temperature ranging from about 220° to about 265° C.

4. The process of claim 1, wherein the molar ratio of olefins in the feed stream to the linear polyaromatic compound ranges from greater than 1:1 to 7:1.

5. The process of claim 1, wherein the linear polyaromatic compound-linear alpha olefin adduct is dissociated by heating the linear polyaromatic compound-linear alpha olefin adduct to a temperature ranging from about 250° C. to 400° C.

6. The process of claim 5, wherein the linear polyaromatic compound-linear alpha olefin adduct is heated to a temperature ranging from about 300° C. to 350° C.

7. The process of claim 1, wherein the separations are carried out by vacuum or flash distillation.

8. The process of claim 1, wherein the separations in step b) or d) are carried out by first cooling followed by filtration or centrifugation.

9. The process of claim 1, wherein the feed stream comprises 1 wt. % or more of branched alpha olefins.

10. The process of claim 1, wherein the feed stream is contacted with 2,3-benzanthracene.

11. The process of claim 1, wherein steps a)–c) are repeated more than once.

12. The process of claim 1, wherein the feed stream contains from 5 wt. % to 85 wt. % branched alpha olefins, and the amount of branched alpha olefins in the linear alpha olefin composition after one pass is less than 4 wt. %.

13. The process of claim 12, wherein the linear polyaromatic compound comprises 2,3-benzanthracene.

14. The process of claim 13, wherein the steps a)–c) are repeated more than once, and the amount of branched alpha olefins is 3.0 wt. % or less.

15. The process of claim 1, wherein the feed stream comprises at least 5 wt. % to 97 wt. % of linear alpha olefins.

16. The process of claim 1, wherein the feed stream comprises at least 20 wt. % to 97 wt. % of linear alpha olefins.

17. The process of claim 1, wherein the average carbon number of the feed stream olefins ranges from 4 to 18.

18. The process of claim 17, wherein the average carbon number of the feed stream olefins ranges from 6 to 18.

19. The process of claim 1, wherein the amount of branched alpha olefin in the feed stream is at least 3 wt. %.

* * * * *